US006197257B1

United States Patent
Raskas

(12) United States Patent
(10) Patent No.: US 6,197,257 B1
(45) Date of Patent: Mar. 6, 2001

(54) MICRO SENSOR DEVICE

(75) Inventor: Eric J. Raskas, St. Louis, MO (US)

(73) Assignee: Microsense of St. Louis, LLC, St. Louis, MO (US)

( * ) Notice: Subject to any disclaimer, the term of this patent is extended or adjusted under 35 U.S.C. 154(b) by 0 days.

(21) Appl. No.: 09/143,258

(22) Filed: Aug. 20, 1998

(51) Int. Cl.[7] .................................................. G01N 21/63
(52) U.S. Cl. .................................. 422/82.05; 422/82.11; 436/95
(58) Field of Search .................................. 422/56, 82.05, 422/82.09, 82.11; 356/39; 600/583, 584; 436/95

(56) References Cited

U.S. PATENT DOCUMENTS

| | | | |
|---|---|---|---|
| 4,637,403 | * 1/1987 | Garcia et al. | 128/770 |
| 5,029,583 | * 7/1991 | Meserol et al. | 422/82.09 |
| 5,341,805 | 8/1994 | Stavridi et al. | 128/633 |
| 5,361,314 | 11/1994 | Kopelman et al. | 385/12 |
| 5,398,681 | 3/1995 | Kupershmidt | 128/633 |
| 5,448,992 | 9/1995 | Kupershmidt | 128/633 |
| 5,529,755 | 6/1996 | Higashio et al. | 422/82.09 |
| 5,533,509 | 7/1996 | Koashi et al. | 128/633 |
| 5,553,613 | 9/1996 | Parker | 128/633 |
| 5,553,616 | 9/1996 | Ham et al. | 128/633 |
| 5,617,852 | 4/1997 | MacGregor | 128/633 |
| 5,627,922 | 5/1997 | Kopelman et al. | 385/12 |
| 5,695,949 | * 12/1997 | Galen et al. | 422/56 |
| 5,846,486 | * 12/1998 | Pugh | 422/56 |
| 5,879,367 | * 3/1999 | Latterell et al. | 606/181 |

OTHER PUBLICATIONS

Analytical Properties and Sensor Size Effects of a Micrometer–Sized Optical Fiber Glucose Biosensor, Zeev Rosenweig and Raoul Kopelman, Analytical Chemistry, vol. 68, No. 8, Apr. 15, 1996, pp. 1408–13.

Dermal Interstitial Glucose as an Indicator of Ambient Glycemia, F. John Service, Peter C. O'Brien, Steven D. Wise, Sheryl Ness, Suzanne M. LeBlanc, Diabetes Care, vol. 20, No. 9, Sep. 1997, pp. 1426–29.

* cited by examiner

*Primary Examiner*—Jeffrey Snay
(74) *Attorney, Agent, or Firm*—Thompson Coburn LLP

(57) ABSTRACT

A micro sensor device for measuring a concentration of a substance within a sample comprises an integrated sensor head having a tip portion adapted to be inserted into a sample, a light source for emitting a beam of light into and through the tip portion with the tip portion capable of interacting with a substance within a sample to produce a reflected pattern of light, and a detector for receiving the reflected pattern of light, and a body portion coupled to the integrated sensor head, the body portion comprising a processor operatively connected to the light source and the detector, the processor for controlling the light source for emitting the beam of light, for receiving the pattern of reflected light from the detector, and for processing the reflected pattern of light to determine the concentration of a substance within a sample.

18 Claims, 2 Drawing Sheets

MICRO SENSOR DEVICE

BACKGROUND OF THE INVENTION

This invention relates generally to a sensor device and more particularly to a micro sensor device which may be employed in a variety of sensor applications to monitor, sense, or measure a concentration of a material within a sample.

There are numerous applications in which a device is used to monitor or detect a concentration of material within a substance. For example, it may be required to know the concentration of a chemical in a sample of material such as knowing the concentration of sodium, calcium, or some other chemical composition in a sample. Monitoring or detecting a concentration of a substance typically requires a set up of relatively complex, sensitive, and expensive equipment or instrumentation. Sometimes space requirements make it difficult to use the set up of complex equipment and it would be advantageous to have equipment which has small dimensions and is easily transportable. Additionally, such complex equipment may not provide results which are of a high resolution.

One known and important application for monitoring a concentration of a material within a sample deals with checking blood glucose for diabetics. There are at least two known techniques for monitoring blood glucose levels in humans. The first technique is invasive which involves extracting samples with the use of needles or syringes. Typically, for the invasive method, a patient employs a small lancet device which is used to prick or puncture a finger. Blood is then collected onto a strip which has incorporated therein a chemical reagent. The strip is then placed inside of a device that optically reads the chemical reaction of the blood on the strip and converts this to a blood glucose level. It has been found very important to control glucose levels in diabetics to reduce any complications associated with diabetes. Many samples or finger pricks may be required to be taken for analysis during the course of a day. Self monitoring of blood glucose by a patient is therefor very important in the treatment of diabetes. Since finger pricking or lancing is required for self monitoring levels of glucose in a patient, many patients avoid this because it is painful and inconvenient. Therefore, a less invasive procedure would be desirable. The second technique is known as noninvasive and does not require that the skin be punctured. The noninvasive technique typically involves a devices which uses near infrared light to detect blood glucose levels. These devices measure a glucose concentration in blood or an organism's tissue by use of an optical device without the need to collect blood or fracturing a part of the organism's tissue. Although these devices use noninvasive methods, in that no blood is collected, none of these devices have been commercially accepted or viable.

The present invention is designed to obviate and overcome many of the disadvantages and shortcomings associated with the prior use of complex testing and monitoring equipment. Additionally, the present invention is simple to use, provides extremely quick results and high resolution, and is easily transportable. The present invention uses relatively inexpensive components which results in a commercially viable product. Further, the micro sensor device of the present invention is relatively noninvasive since it does not require the drawing of blood and provides immediate results which does not require related blood processing such as centrifugation, storage, transportation, and other time consuming testing.

SUMMARY OF THE INVENTION

The present invention is a micro sensor device for measuring a concentration of a substance within a sample which comprises an integrated sensor head having a tip portion adapted to be inserted into a sample, a light source for emitting a beam of light into and through the tip portion with the tip portion capable of interacting with a substance within a sample to produce a reflected pattern of light, and a detector for receiving the reflected pattern of light, and a body portion coupled to the integrated sensor head, the body portion comprising a processor operatively connected to the light source and the detector, the processor for controlling the light source for emitting the beam of light, for receiving the pattern of reflected light from the detector, and for processing the reflected pattern of light to determine the concentration of a substance within a sample.

Another example of the present invention is a micro sensor device for measuring a concentration of a substance within a sample which comprises a first integrated sensor head having a tip portion adapted to be inserted into a sample, a second integrated sensor head coupled to the first integrated sensor head, the second integrated sensor head comprising a light source for emitting a beam of light into and through the first integrated sensor head and the tip portion with the tip portion capable of interacting with a substance within a sample to produce a reflected pattern of light, and a detector for receiving the reflected pattern of light, and a body portion coupled to the second integrated sensor head, the body portion comprising a processor operatively connected to the light source and the detector, the processor for controlling the light source for emitting the beam of light, for receiving the pattern of reflected light from the detector, and for processing the reflected pattern of light to determine the concentration of a substance within a sample.

A further example of the present invention is a micro sensor device for measuring a concentration of at least two different substances within a sample comprising an integrated sensor head having a tip portion adapted to be inserted into a sample, a light source for emitting a beam of light into and through the tip portion with the tip portion capable of interacting with at least two different substances within a sample to produce a first pattern of reflected light and a second pattern of reflected light, and a first detector for receiving the first pattern of reflected light and a second detector for receiving the second pattern of reflected light, and a body portion coupled to the integrated sensor head, the body portion comprising a processor operatively connected to the light source and the detectors, the processor for controlling the light source for emitting the beam of light, for receiving the patterns of reflected light from the detectors, and for processing the patterns of reflected light to determine the concentration of at least two different substances within a sample.

In light of the foregoing comments, it will be recognized that a principal object of the present invention is to provide an improved sensor device which is hand held, portable, and easy to operate.

Another object of the present invention is to provide a sensor device which has a tip portion of an extremely small size so that when it is inserted into a hand of a patient little or no sensation will be produced or detected.

A further object of the present invention is to provide a sensor device which is of simple construction and design and which can be easily employed with highly reliable results.

Another object of the present invention is to provide a sensor device which is accurate and provides readings in a short time period.

A still further object of the present invention is to provide a sensor device which is compact in design and is easily transportable for personal use.

Another object of the present invention is to provide a sensor device having a tip portion which interfaces to electronic components without using any optical interconnects or optical splitter devices.

A further object of the present invention is to provide a sensor device which contains few parts or components and is easy to fabricate or construct.

These and other objects and advantages of the present invention will become apparent after considering the following detailed specification in conjunction with the accompanying drawings, wherein:

DETAILED DESCRIPTION OF THE PREFERRED EMBODIMENTS

Figure 1:
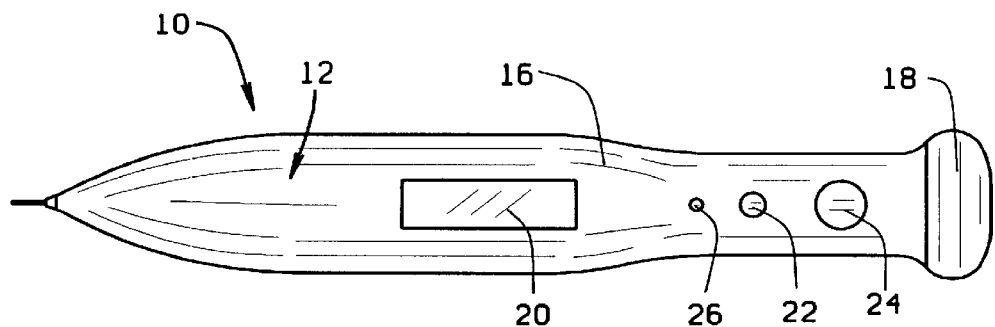
FIG. 1 is a perspective view of a micro sensor device constructed according to the present invention.

Referring now to the drawings, wherein like numbers refer to like items, number 10 identifies a preferred embodiment of a micro sensor device constructed according to the present invention. As illustrated in FIG. 1, the device 10 comprises a pencil or pen shaped body 12 which includes an integrated sensor head 14, a central body portion 16, and an end cap 18. The central body portion 16 further includes a display device 20, such as an LED (light emitting diode) type display or an LCD (liquid crystal display) type display, for displaying information. The end cap 18, which may be removable from the central body portion 16, is used to allow access into the interior of the central body portion 16. Batteries (not shown) can be inserted into the central body portion 16 to supply power to the device 10, as will be explained. The central body portion 16 may also include an ON/OFF switch 22 which may be used to operate the device 10, a speaker 24 which may be to audibly indicate certain information, and an LED 26 which may be used to indicate that a reading has been completed. Other switches (not shown) may be incorporated into the central body portion 16 to further control the device 10. Additionally, the central body portion 16 houses electronic circuitry and other components which will be illustrated and explained in further detail herein. The device 10 is sized and shaped to be a hand held type device which is portable and preferably is the size and shape of a pencil or a pen.

Figure 2:
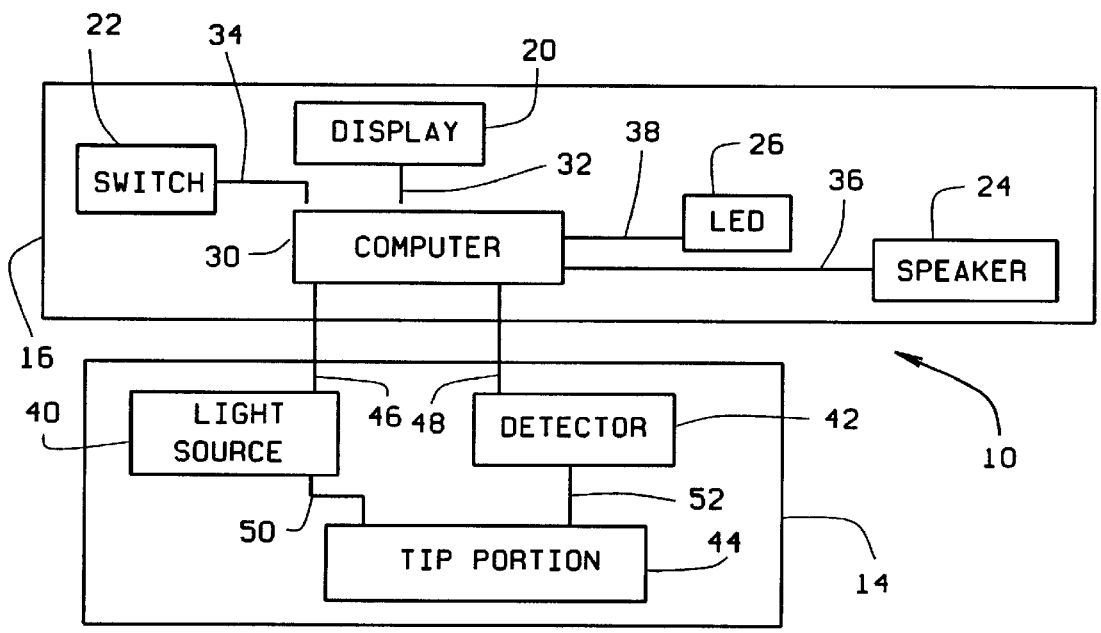
FIG. 2 is a block diagram of the micro sensor device constructed according to the present invention.

With reference now to FIG. 2, a block diagram of the circuitry and components of the device 10 is shown. The device 10 includes a computer 30 which is connected to the display 20 by a wire 32, to the switch 22 by a wire 34, to the speaker 24 by a wire 36, and to the LED 26 by a wire 38. The computer 30 may consists of, by way of examples, a microprocessor, a microcontroller, an ASIC chip, or any other known equivalent device which is capable of processing electrical signals. The computer 30 may also be connected to a power supply, such as a battery, although the power supply and such connection are not illustrated in FIG. 2. Additionally, the computer 30 may also be connected to other switches (not shown) which may be provided with the device 10 to further control or operate the device 10. The computer 30 and the other components 20, 22, 24, and 26 are all housed within the central body portion 16.

The integrated sensor head 14 comprises a light source 40, a detector 42, and a tip portion 44 all incorporated or integrated within the integrated sensor head 14. For example, the integrated sensor head 14 may be formed by any suitable injection molding method or technique. Additionally, the integrated sensor head 14 is of an extremely small size on the order of about under 30 microns in size. The light source 40 is operatively connected to the computer 30 by an electrical connection 46 and the detector 42 is likewise electrically connected to the computer 30 by an electrical connection 48. The tip portion 44 consists of an extremely small needle shaped analyte. The light source 40 may be an LED, a laser, a laser diode, or other light excitation source. The light source 40 is adapted to project a beam of light 50 into the tip portion 44. The beam of light 50 passes through the tip portion 44 and a reflected pattern of light 52 may be reflected back from a sample (not shown) through the tip portion 44 to the detector 42. The detector 42 provides the reflected pattern of light 52 to the computer 30 for processing to determine the concentration of material within a sample. The detector 42 may be, for example, a photodiode, a miniature spectrometer, or any other device which may detect light.

Figure 3:
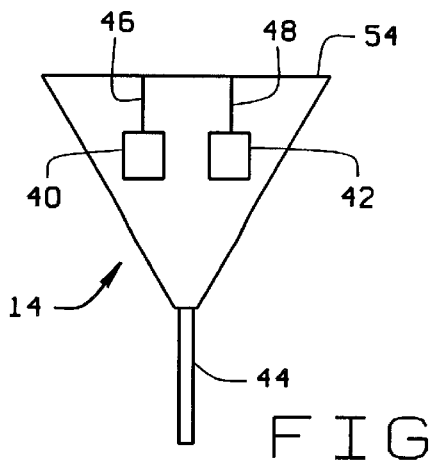
FIG. 3 is a perspective view of a tip portion of the micro sensor device shown in FIG. 1.

The integrated sensor head 14 is shown in greater detail in FIG. 3 and again is preferably a small device on the order of under 30 microns in size or diameter. In particular, the sensor head 14 is of unitary construction having the light source 40, detector 42, and tip portion 44 incorporated therein. The electrical connections 46 and 48 extend from the light source 40 and the detector 42, respectively, and terminate at a first end 54 of the sensor head 14. In this manner, the connections 46 and 48 mate with corresponding connections or terminals (not shown) in the central body portion 16. The use of the electrical connections 46 and 48 eliminates any alignment problems which would been associated with other types of connectors, such as an optical connection. Additionally, the sensor head 14 is mated or connected to the central body portion 16 in any suitable manner, as for example by screw type attachment or even frictional engagement.

The tip portion 44 may be chemically treated or use an enzymatic process or treatment which enables the tip portion 44 to interact with the sample to be detected or monitored. Properties of the tip portion 44 may vary dependent upon the sample and the chemical or substance to be detected by the device 10. As constructed and with particular reference to FIG. 2, the tip portion 44 allows for the beam of light 50 to pass through and the reflected pattern of light 52 to be reflected through the tip portion 44. As indicated above, the tip portion 44 is extremely small and because of its size it can be inserted through gaps inbetween most cells or through the membrane of a cell without damaging the cell. Additionally, the tip portion is small enough that when it is inserted into a human, for example a human hand, there will be little or no sensation felt.

The tip portion 44 may have specific chemical sensitivities based upon the properties of a dye matrix. A dye may be chemically activated by a different chemical compound which enables sensing of a specific chemical property within a sample or a substance. The tip portion 44 provides for enhanced sensitivity, selectivity, and stability when detecting a concentration within a sample or substance. In this manner, the sensor device 10 interacts with the substance or sample to detect a specific chemical or concentration within the substance. Some examples of how the tip portion 44 may be chemically treated to have specific chemical sensitivities or to interact with the sample to be detected or monitored may be found in U.S. Pat. Nos. 5,361,314 and 5,627,922.

Figure 4:
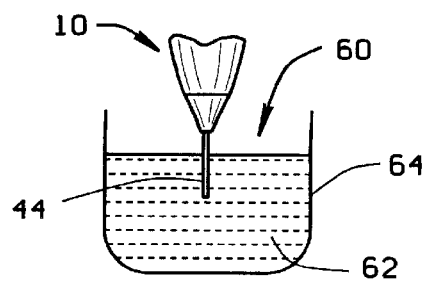
FIG. 4 is a schematic view of the micro sensor device of the present invention being employed to sense a concentration in a sample.

With reference now to FIGS. 1, 2, and 4, the operation of the device 10 will be explained in detail. In order to operate the device 10, the on/off switch 22 is pressed to initialize the device 10. Once powered, the device 10 may be inserted into a sample 60 to test for a particular concentration of material within the sample 60. As shown in FIG. 4, the sample to be tested is a liquid 62 in a beaker 64. The tip portion 44 is inserted into the liquid 62 and at this point in time a beam of light, such as the beam of light 50, is transmitted into the liquid 62. With the tip portion 44 being in contact with the liquid 62, the liquid 62 reacts chemically with the tip portion 44 and the color of the chemical composing the sensor device 10 changes. As a result of this change, the pattern of the light reflected back into the tip portion 44 changes, such as that shown by the pattern of reflected light 52. This pattern is sensed by the detector 42 and signals are provided to the computer 30 which performs a calculation to determine the concentration of the particular chemical being sensed and the result may be displayed in the display 20.

Additionally, the chemical properties of the tip portion 44 of the sensor portion 14 may be changed to react with another chemical to detect some other chemical within a sample. Further, instead of changing the chemical properties of the tip portion 44, it may only be necessary to change the light source 40 to detect some other chemical within a sample. It is also possible to have a cap (not shown) which covers the tip portion 44 when the device 10 is not in use. The cap may also have incorporated therein a mechanism for keeping the tip portion 44 sterilized.

The tip portion 44 may be constructed by using any suitable injection molding method or technique and precision injection molding methods for molding extremely small parts may be employed. Another method or technique for constructing the tip portion 44 may include a micro fabrication process known as micro-electro-mechanical systems (MEMS) fabrication process wherein an extremely small sized part may be carved out of a substance. Even a micro-opto-electro-mechanical system (MOEMS) may be used to produce the tip portion 44. Additionally, the tip portion 44 may be manufactured from silicas, plastics, polymers, or even pyrex. Other known methods for construction of the tip portion may be a heat drawn process or even swaging.

Figure 5:
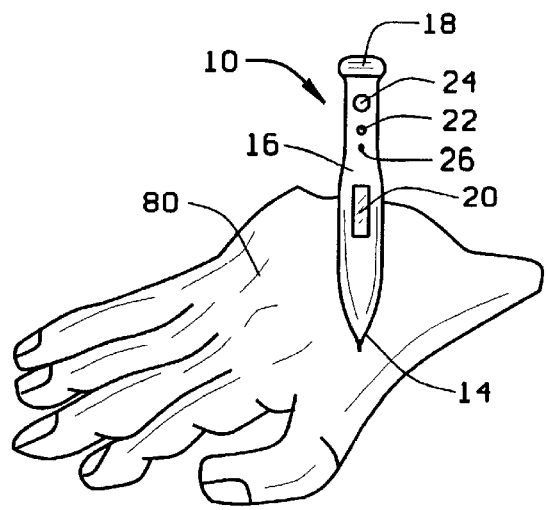
FIG. 5 is perspective view of the micro sensor device of FIG. 1 illustrated monitoring a concentration of glucose in a hand of a patient.

Referring now to FIG. 5, the sensor device 10 is again shown having a pencil like body 12 which includes the central body portion 16, the end cap 18, and the sensor head 14 which has been inserted into a hand 80 in order to detect the presence of a concentration of material, such as for example glucose. The central body portion 16 includes the display 20 for displaying information such as glucose concentration, the ON/OFF switch 22 for operating the device 10, the speaker 24, and the LED 26. The tip portion 14 is shown being inserted into the hand 80 and because of its extremely small size little or no sensation will be felt. The other components of the sensor device 10, which were discussed with reference to FIG. 2, are all housed within the central body portion 16 and the tip portion 14.

Once inserted into the hand 80, actuation of the sensor device 10 will cause the computer 30 to operate the light source 40. The light beam 50 is produced and sent through the tip portion 44. With the tip portion 44 being in contact with the hand 80, the tip portion 44 reacts chemically and the pattern of light 52 is generated and reflected back through the tip portion 44 to the detector 42. The detector 42 transmits the pattern of light 52 to the computer 30 which then calculates the concentration of glucose within the hand 80. The result may be displayed in the display 20 or audibly indicated by the speaker 24. Once the result is indicated the device 10 may be removed from the hand 80 and turned off.

Figure 6:
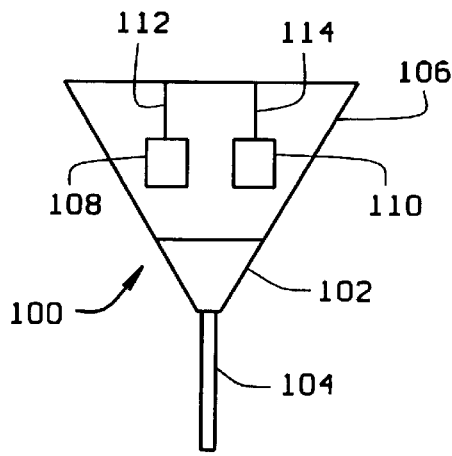
FIG. 6 is a block diagram of another embodiment of the integrated sensor head constructed according to the present invention.

FIG. 6 illustrates another embodiment of an integrated sensor head 100 which may be used with the device 10. The sensor head 100 comprises a first integrated portion 102 which includes a tip portion 104 and a second integrated portion 106 which includes a light source 108, a detector 110, and connectors 112 and 114 which are connected to the light source 108 and the detector 110, respectively. The first integrated portion 102 may be connected to the second integrated portion 106 by any suitable method or constructions, such as by a screw type construction. In this embodiment the first integrated portion 102 is easily removable from the second integrated portion 106 and the first integrated portion 102 may be interchanged with new first integrated portions 102 as need be. For example, the tip portion 104 of the first integrated portion 102 may lose its effectiveness over time, degrade, or become contaminated and removal of the first integrated portion 102 is all that will be required to change to a new tip portion 104. In this manner, the sensor head 100 has the feature of a replaceable tip portion 104. Additionally, the first integrated portion 102 including the tip portion 104 is disposable and easily discarded from second integrated portion 106. The second tip portion 106 incorporates the light source 108, the detector 110, and the connectors 112 and 114 and there is no need to replace these elements 106–114 in this embodiment.

Figure 7:
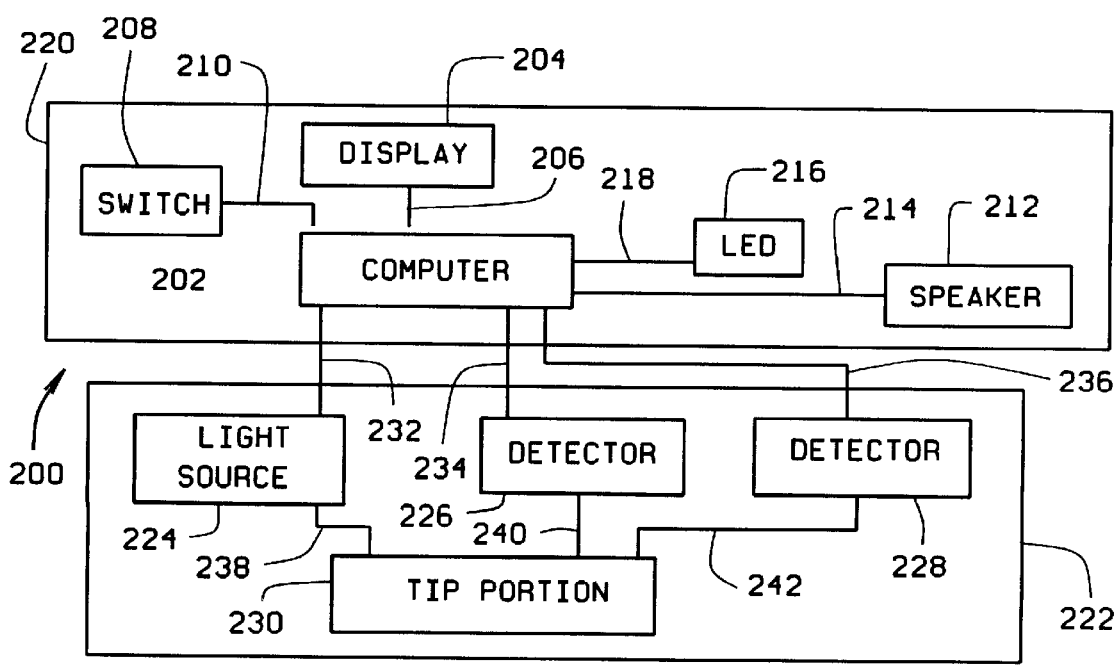
FIG. 7 is a block diagram of a second embodiment of the micro sensor device constructed according to the present invention.

FIG. 7 depicts a block diagram of another embodiment of a micro sensor device 200. The sensor device 200 comprises a computer 202 which is connected to a display device 204 by a wire 206. to a power switch 208 by a wire 210, to a speaker 212 by a wire 214, and to an LED 216 by a wire 218. The computer 202 may consists of, by way of examples, a microprocessor, a microcontroller, an ASIC chip, or any other known equivalent device which is capable of processing electrical signals and controlling various output devices or components. The computer 202 may also be connected to a power supply, such as a battery or a rechargeable battery although the power supply and such connection are not illustrated in FIG. 7. Additionally, the computer 202 may also be connected to other switches (not shown) which may be provided with the device 200 to further control or operate the device 200. The computer 202 and the other components 204, 208, 212, and 216 are all housed within a central body portion 220 of the device 200.

An integrated sensor head 222 is connected to the central body portion 220 by any suitable means. The integrated sensor head 222 comprises a light source 224, a first detector 226, a second detector 228, and a tip portion 230 all incorporated or integrated within the integrated sensor head 222. For example, the integrated sensor head 14 may be formed by any suitable injection molding method or technique. Additionally, the integrated sensor head 222 is of an extremely small size on the order of about under 30 microns in size. The light source 224 is operatively connected to the computer 202 by an electrical connection 232 and the first detector 226 is likewise electrically connected to the computer 202 by an electrical connection 234. The second detector 228 is also connected or interfaced to the computer 202 by a connection 236. The tip portion 230 consists of an extremely small needle shaped analyte. The light source 224 may be an LED, a laser, a laser diode, or other light excitation source. The light source 224 is adapted to project a beam of light 238 into the tip portion 230. The beam of light 238 passes through the tip portion 230 and a first reflected pattern of light 240 may be reflected back from a sample (not shown) through the tip portion 230 to the first detector 226. The first detector 226 provides the first reflected pattern of light 240 to the computer 202 via the connection 234 for processing to determine the concentration of material within a sample. Additionally, a second reflected pattern of light 242 may be produced and reflected back from a sample (not shown) through the tip portion 230 to the second detector 228. The second detector 228 provides the second reflected pattern of light 242 to the computer 202 via the connection 236 for processing to determine the concentration of material within a sample. Examples of the first detector 226 and the second detector 228 were previously noted above with respect to the detector 42. In this manner, two different substances may be monitored or detected by the device 200. Although the device 200 is depicted to show the monitoring of at least two different chemical compounds or substances it is also contemplated that more than two chemical compounds or substances may be sensed, detected, or monitored by the device 200 by adding additional components, as has been taught and illustrated.

Although not illustrated, it is also possible and contemplated to have an integrated head sensor which has the light source 224 and the two detectors 226 and 228 incorporated within a first integrated head portion and the tip portion 230 incorporated within a second integrated head portion which is separable from the first integrated head portion. In this manner, the second integrated head portion in essence becomes a disposable component of the micro sensor device.

From all that has been said, it will be clear that there has thus been shown and described herein a micro sensor device which fulfills the various objects and advantages sought therefor. It will be apparent to those skilled in the art, however, that many changes, modifications, variations, and other uses and applications of the subject micro sensor device are possible and contemplated. All changes, modifications, variations, and other uses and applications which do not depart from the spirit and scope of the invention are deemed to be covered by the invention, which is limited only by the claims which follow.

What is claimed is:

1. A micro sensor device for measuring a concentration of a substance within a sample comprising:
    at least one integrated sensor head module having a tip portion being sized and adapted to be inserted into a sample through intercellular gaps or through a cell membrane, said module including a light source for emitting a beam of light into and through the tip portion, said tip portion being capable of transmitting light and having an exterior surface treated to interact with a substance within a sample to produce a reflected pattern of light, said module further including a detector for receiving the reflected pattern of light; and
    a body portion coupled to the integrated sensor head module, the body portion comprising a processor operatively coupled to the light source and the detector, the processor for controlling the light source for emitting the beam of light, for receiving the pattern of reflected light from the detector, and for processing the reflected pattern of light to determine the concentration of a substance within a sample.

2. The micro sensor device of claim 1 wherein the concentration to be measured is glucose and the sample is a human.

3. The micro sensor device of claim 1 wherein the tip portion of the integrated sensor head is formed by a micro machining process.

4. The micro sensor device of claim 1 further comprising audible means for audibly indicating the concentration of a substance within a sample.

5. The micro sensor device of claim 1 wherein the integrated sensor head is removably coupled to the body portion.

6. The micro sensor device of claim of claim 1 wherein the integrated sensor head is formed by injection molding.

7. A micro sensor device for measuring a concentration of a substance within a sample comprising:
    a first integrated sensor head module having a tip portion being sized and adapted to be inserted into a sample through intercellular gaps or through a cell membrane;
    a second integrated sensor head module coupled to the first integrated sensor head module, the second integrated sensor head module comprising a light source for emitting a beam of light into and through the first integrated sensor head module and the tip portion being capable of transmitting light and having an exterior surface treated to interact with a substance within a sample to produce a reflected pattern of light, and a detector for receiving the reflected pattern of light; and
    a body portion coupled to the second integrated sensor head module, the body portion comprising a processor operatively coupled to the light source and the detector, the processor for controlling the light source for emitting the beam of light, for receiving the pattern of reflected light from the detector, and for processing the reflected pattern of light to determine the concentration of a substance within a sample.

8. The micro sensor device of claim 7 wherein the concentration to be measured is glucose and the sample is a human.

9. The micro sensor device of claim 7 wherein the tip portion of the first integrated sensor head is formed by a micro machining process.

10. The micro sensor device of claim 7 further comprising audible means for audibly indicating the concentration of a substance within a sample.

11. The micro sensor device of claim 7 wherein the first integrated sensor head is removably coupled to the second integrated sensor head.

12. The micro sensor device of claim 7 wherein the first and second integrated sensor heads are formed by injection molding.

13. A micro sensor device for measuring a concentration of at least two different substances within a sample comprising:

an integrated sensor head module having a tip portion being sized and adapted to be inserted into a sample through intercellular gaps or through a cell membrane, said module including a light source for emitting a beam of light into and through the tip portion, said tip portion being capable of transmitting light and having an exterior surface treated to interact with at least two different substances within a sample to produce a first pattern of reflected light and a second pattern of reflected light, said module further including a first detector for receiving the first pattern of reflected light and a second detector for receiving the second pattern of reflected light; and a body portion coupled to the integrated sensor head module, the body portion comprising a processor operatively coupled to the light source and the detector, the processor for controlling the light source for emitting the beam of light, for receiving the pattern of reflected light from the detector, and for processing the reflected pattern of light to determine the concentration of a substance within a sample.

14. The sensor device of claim 13 wherein the first substance to be measured is glucose and the sample is a human.

15. The sensor device of claim 13 wherein the tip portion is formed by a micro machining process.

16. The sensor device of claim 13 further comprising audible means for audibly indicating the concentration of the first substance within a sample.

17. The sensor device of claim 13 wherein the integrated head portion is removably coupled to the body portion.

18. The sensor device of claim 13 wherein the integrated sensor head is formed by injection molding.

* * * * *